(12) United States Patent
Hillman

(10) Patent No.: US 7,713,243 B2
(45) Date of Patent: May 11, 2010

(54) TIP SHIELD FOR NEEDLE STICK PREVENTION

(75) Inventor: Jason Hillman, West Jordan, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 173 days.

(21) Appl. No.: 11/861,085

(22) Filed: Sep. 25, 2007

(65) Prior Publication Data

US 2009/0082732 A1   Mar. 26, 2009

(51) Int. Cl.
*A61M 5/32* (2006.01)
(52) U.S. Cl. .................................. 604/192
(58) Field of Classification Search ............ 604/162, 604/164.08, 110, 111, 161, 192
See application file for complete search history.

(56) References Cited

U.S. PATENT DOCUMENTS

| | | | |
|---|---|---|---|
| 4,755,170 A | | 7/1988 | Golden |
| 4,952,207 A | | 8/1990 | Lemieux |
| 4,964,854 A | | 10/1990 | Luther |
| 4,978,344 A | | 12/1990 | Dombrowski et al. |
| 5,053,017 A | | 10/1991 | Chamuel |
| 5,085,648 A | | 2/1992 | Purdy et al. |
| 5,120,309 A | * | 6/1992 | Watts .................. 604/110 |
| 5,135,504 A | | 8/1992 | McLees |
| 5,183,468 A | * | 2/1993 | McLees .............. 604/164.08 |
| 5,215,528 A | | 6/1993 | Purdy et al. |
| 5,242,425 A | * | 9/1993 | White et al. ............... 604/256 |
| 5,533,974 A | * | 7/1996 | Gaba ...................... 604/110 |
| 5,558,651 A | | 9/1996 | Crawford et al. |
| 5,601,536 A | * | 2/1997 | Crawford et al. ........... 604/263 |
| 5,683,365 A | | 11/1997 | Brown et al. |
| 5,738,660 A | * | 4/1998 | Luther ................. 604/164.08 |
| 5,792,122 A | * | 8/1998 | Brimhall et al. ............ 604/263 |
| 5,833,670 A | | 11/1998 | Dillon et al. |
| 5,879,337 A | | 3/1999 | Kuracina et al. |
| 6,001,080 A | | 12/1999 | Kuracina et al. |
| 6,004,294 A | | 12/1999 | Brimhall et al. |
| 6,012,213 A | | 1/2000 | Chang et al. |
| 6,117,108 A | | 9/2000 | Woehr et al. |
| 6,197,001 B1 | * | 3/2001 | Wilson et al. ............... 604/157 |
| 6,224,569 B1 | | 5/2001 | Brimhall |
| 6,280,419 B1 | | 8/2001 | Vojtasek |
| 6,287,278 B1 | | 9/2001 | Woehr et al. |
| 6,322,537 B1 | | 11/2001 | Chang |

(Continued)

*Primary Examiner*—Nicholas D Lucchesi
*Assistant Examiner*—Diva Ranade
(74) *Attorney, Agent, or Firm*—Mony R. Ghose; Craig Metcalf; Kirton & McConkie

(57) ABSTRACT

A vascular access system for preventing needle sticks includes a needle, a tip shield, and a housing. The needle may be a hypodermic needle or other conventional needle having a needle shaft terminating at a needle tip. The tip shield provides an enclosure defining a chamber. The enclosure includes a closed distal end and a proximal end that slidably engages the needle shaft. The enclosure further includes at least one side wall configured to slidably engage the needle shaft. The housing defines a passageway with respective proximal and distal openings through which the needle extends. The tip shield is also disposed in the passageway and is releasably retained therein. The needle and/or the tip shield is adapted to prevent the needle shaft from being completely withdrawn from the tip shield. The tip shield further secures the needle tip in the chamber upon withdrawal of the needle tip into the chamber.

17 Claims, 8 Drawing Sheets

U.S. PATENT DOCUMENTS

| | | | |
|---|---|---|---|
| 6,379,333 B1 | 4/2002 | Brimhall et al. | |
| 6,443,927 B1 | 9/2002 | Cook | |
| 6,443,929 B1 | 9/2002 | Kuracina et al. | |
| 6,595,954 B1 | 7/2003 | Luther et al. | |
| 6,616,630 B1 * | 9/2003 | Woehr et al. | 604/110 |
| 6,616,638 B2 * | 9/2003 | Peters, III | 604/192 |
| 6,629,959 B2 * | 10/2003 | Kuracina et al. | 604/192 |
| 6,652,486 B2 | 11/2003 | Bialecki et al. | |
| 6,652,490 B2 | 11/2003 | Howell | |
| 6,663,592 B2 | 12/2003 | Rhad et al. | |
| 6,689,102 B2 * | 2/2004 | Greene | 604/164.08 |
| 6,692,471 B2 | 2/2004 | Boudreaux | |
| 6,749,588 B1 | 6/2004 | Howell et al. | |
| 6,761,706 B2 | 7/2004 | Vaillancourt | |
| 6,860,871 B2 | 3/2005 | Kuracina et al. | |
| 6,914,212 B2 | 7/2005 | Adams | |
| 6,942,643 B2 * | 9/2005 | Eakins et al. | 604/111 |
| 7,002,098 B2 | 2/2006 | Adams | |
| 7,029,461 B2 * | 4/2006 | Ferguson et al. | 604/198 |
| 7,112,191 B2 * | 9/2006 | Daga | 604/263 |
| 7,160,269 B2 | 1/2007 | Woehr | |
| 7,214,208 B2 | 5/2007 | Vaillancourt | |
| 7,214,211 B2 | 5/2007 | Woehr et al. | |
| 7,238,169 B2 | 7/2007 | Takagi et al. | |
| 7,264,613 B2 | 9/2007 | Woehr et al. | |
| 7,347,838 B2 * | 3/2008 | Kulli | 604/164.08 |
| 7,361,160 B2 * | 4/2008 | Hommann et al. | 604/198 |
| 7,396,346 B2 * | 7/2008 | Nakajima | 604/167.03 |
| 2003/0220614 A1 * | 11/2003 | Crawford | 604/192 |
| 2004/0186434 A1 | 9/2004 | Harding et al. | |
| 2004/0204687 A1 | 10/2004 | Mogensen et al. | |
| 2004/0225260 A1 | 11/2004 | Villa et al. | |
| 2004/0243061 A1 | 12/2004 | McGurk | |
| 2005/0027263 A1 | 2/2005 | Woehr et al. | |
| 2005/0080378 A1 * | 4/2005 | Cindrich et al. | 604/164.01 |
| 2006/0116638 A1 | 6/2006 | Woehr et al. | |
| 2006/0155245 A1 | 7/2006 | Woehr | |
| 2006/0270980 A1 | 11/2006 | Menzi et al. | |
| 2007/0038186 A1 * | 2/2007 | Sutton et al. | 604/164.08 |
| 2007/0073221 A1 | 3/2007 | Bialecki et al. | |
| 2007/0088261 A1 * | 4/2007 | Lew et al. | 604/110 |
| 2007/0100297 A1 | 5/2007 | Woehr et al. | |
| 2007/0112305 A1 | 5/2007 | Brimhall | |
| 2007/0161950 A1 | 7/2007 | Carlyon et al. | |
| 2007/0179446 A1 | 8/2007 | Carrez et al. | |
| 2007/0179447 A1 | 8/2007 | Carrez et al. | |

* cited by examiner

TIP SHIELD FOR NEEDLE STICK PREVENTION

BACKGROUND OF THE INVENTION

This disclosure relates generally to vascular access systems and methods, including hypodermic needles, needle assemblies, catheter assemblies, and devices used with catheter assemblies. Generally, vascular access systems are used for communicating fluid with the vascular system of patients and may include one or more vascular access devices. For example, catheters are used for infusing fluid, such as saline solution, various medicaments, and/or total parenteral nutrition, into a patient, withdrawing blood from a patient, and/or monitoring various parameters of the patient's vascular system.

Intravenous (IV) catheter assemblies are among the various types of vascular access systems, and over-the-needle peripheral IV catheters are a common IV catheter configuration. As its name implies, an over-the-needle catheter is mounted over an introducer needle having a sharp distal tip. The introducer needle is generally a hypodermic needle forming a part of a needle assembly to help guide the needle and to facilitate its cooperation with the catheter. At least the inner surface of the distal portion of the catheter tightly engages the outer surface of the needle to prevent peelback of the catheter and thus facilitates insertion of the catheter into the blood vessel. The catheter and the introducer needle are assembled so that the distal tip of the introducer needle extends beyond the distal tip of the catheter with the bevel of the needle facing up away from the patient's skin. The catheter and introducer needle are generally inserted at a shallow angle through the patient's skin into a blood vessel.

In order to verify proper placement of the needle and/or catheter in the blood vessel, the clinician generally confirms that there is "flashback" of blood in a flashback chamber, which is generally associated with a needle assembly. Once proper placement of the distal tip of the catheter into the blood vessel is confirmed, the clinician may apply pressure to the blood vessel by pressing down on the patient's skin over the blood vessel distal of the introducer needle and the catheter. This finger pressure occludes the vessel, minimizing further blood flow through the introducer needle and the catheter.

The clinician may then withdraw the introducer needle from the catheter. The introducer needle may be withdrawn into a needle tip shield or needle shield that covers the needle tip and prevents accidental needle sticks. In general, a needle tip shield includes a housing, a sleeve, or other similar device that is designed such that when the needle is withdrawn from the patient, the needle tip will be trapped/captured within the needle tip shield. The purpose of the needle tip shield is to house the tip of the needle in a secure location, thereby reducing the possibility of needle sticks when the needle and needle tip shield are separated properly from the catheter, which is left in place to provide intravenous access to the patient.

The separation of the needle assembly from the catheter portions of the catheter assembly presents numerous potential hazards to the clinicians and others in the area. As indicated above, there is a risk of accidental needle sticks if the needle tip is not secured properly in a needle tip shield. Additionally, because the needle has been in contact with blood in the patient's vasculature, blood is often present on the exterior of the needle and is often present inside the lumen of the needle. As the needle is withdrawn, there is a risk that this blood will drip from the needle tip or come into contact with other surfaces to expose clinicians and equipment to blood. The present disclosure presents systems and methods to significantly limit and/or prevent needle sticks, and in some implementations, blood exposure.

SUMMARY OF THE INVENTION

The systems and methods of the present disclosure have been developed in response to problems and needs in the art that have not yet been finally resolved by currently available vascular access systems and methods. Thus, these systems and methods are developed to provide safer vascular access systems, methods of manufacturing the same, and methods of using the same to reduce needle sticks.

A vascular access system within the scope of the present invention includes a hypodermic needle, a tip shield, and a housing. The needle includes a needle shaft that terminates at a needle tip. The tip shield includes an enclosure defining a chamber. The enclosure includes at least one side wall configured to slidably engage the needle shaft, a closed distal end, and a proximal end slidably engaging the needle shaft. Accordingly, the tip shield may be disposed at an angle with respect to the needle when the needle extends through both the side wall and the proximal end of the tip shield. The housing of the vascular access system defines a passageway with respective proximal and distal openings through which the needle slidably extends. The proximal opening of the housing releasably retains the tip shield in the passageway. Through a variety of possible implementations, at least one of the needle and the tip shield are adapted to prevent the needle shaft from being completely withdrawn from the tip shield. Additionally, the tip shield is adapted to secure the needle tip in the chamber upon withdrawal of the needle tip into the chamber.

In some implementations, vascular access systems within the scope of the present invention include a needle having an enlarged shaft region proximate to the needle tip. The enlarged shaft region cooperates with and engages an opening in the proximal end of the tip shield adapted to slidably engage the needle shaft without allowing the enlarged region to pass proximally through the opening. Additionally or alternatively, some implementations may include a tip shield having an elongate hollow body defining the chamber and a needle shaft port, which may be in a side wall of the elongate body. In such implementations, the needle shaft extends through the opening in the proximal end of the tip shield and the needle shaft port when the needle is disposed in the housing, which disposes the tip shield at an angle with the needle shaft. The opening in the proximal end of the tip shield may be configured as a pivot hole that engages the enlarged shaft region during proximal movement of the needle relative to the housing and further proximal movement of the needle relative to the housing causes the tip shield to pivot at the pivot hole drawing the needle tip into and through the needle shaft port and into the chamber.

These and other features and advantages of the present disclosure may be incorporated into certain embodiments and will become more fully apparent from the following description and appended claims, or may be learned by the practice of the methods and use of the systems as set forth hereinafter. The present disclosure does not require that all the advantageous features and all the advantages described herein be incorporated into every embodiment.

BRIEF DESCRIPTION OF THE DRAWINGS

In order that the manner in which the above-recited and other features and advantages of the invention are obtained

DETAILED DESCRIPTION

The presently preferred embodiments of the present disclosure will be best understood by reference to the drawings. It will be readily understood that the components of the present disclosure, as generally described and illustrated in the figures herein, could be arranged and designed in a wide variety of different configurations. Thus, the following more detailed description, as represented in the figures, is not intended to limit the scope of the claims, but is merely representative of presently preferred embodiments.

Figure 1:
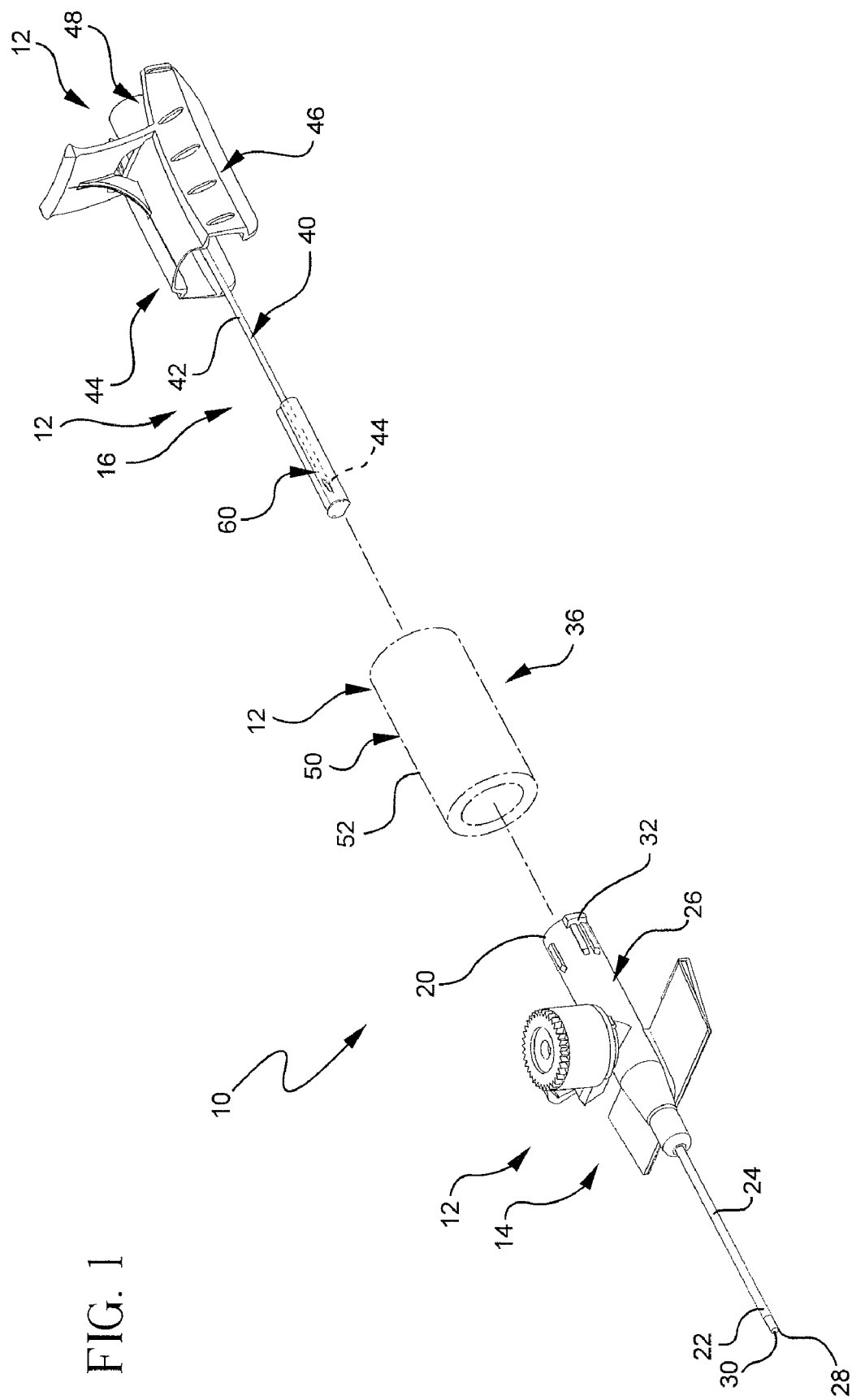
FIG. 1 is an exploded perspective view of an exemplary extravascular system incorporating multiple exemplary vascular access devices.

Referring to FIG. 1, the perspective view illustrates an example of an extravascular system 10, or vascular access system, including multiple vascular access devices 12. In this example, the extravascular system 10 includes a catheter assembly 14 and a needle assembly 16. The catheter assembly 14 has a proximal end 20 and a distal end 22 and includes a catheter 24 having an opening 28 at the distal end 22 of the catheter assembly 14 and a catheter hub 26 disposed at the proximal end 20 of the catheter assembly 14. The catheter assembly 14 also defines a lumen 30 extending from the proximal end 20 to the distal end 22.

Proximal end 20 of catheter assembly 14 may be configured in any suitable manner to facilitate its cooperation with other vascular access devices. Two exemplary configurations are illustrated in FIG. 1. Shown in solid lines in FIG. 1, the catheter assembly proximal end 20 may be configured with positioning ridges and grooves 32 adapted to coordinate with similar features on adjoining devices. The positioning ridges and grooves 32 are examples of coupling systems that may be used to position and/or retain another vascular access device, such as adapters, flow control plugs, dead-ender caps, or other devices (not shown), attached to the catheter hub 26 in a desired orientation. Other suitable coupling and positioning systems may be used. For example, traditional Luer lock features may be included, which may be male or female Luer lock configurations. FIG. 1 further illustrates, in dotted lines, that the catheter assembly 14 may optionally be configured with an activating housing 34 adapted to cooperate with particular aspects of the present vascular access systems. The activating housing 34 will be described in greater detail below, including at least with reference to FIG. 3. The activating housing 34 is one example of a housing 36 within the scope of the present disclosure.

Continuing with FIG. 1, the vascular access system 10 includes a needle assembly 16 includes a hypodermic needle 40 having a needle shaft 42 adapted to extend through the lumen 30 of the catheter assembly 14. The needle tip 44 and other aspects of the needle 40 are obscured in FIG. 1 by the position of the tip shield 60 and will be illustrated and described in connection with subsequent figures. The illustrated needle assembly 16 includes a needle hub 46, which may be provided in some implementations to facilitate the insertion, removal, and control of the needle 40 and the needle assembly 16 generally. The proximal end of the needle assembly 16 may be adapted to cooperate with yet additional vascular access devices 12, such as a flow control plug 48 as illustrated in FIG. 1.

While the needle assembly 16 illustrated in FIG. 1 is configured for use with the catheter assembly 14, other needle assemblies and vascular access systems within the scope of the present invention may include hypodermic needles (not shown) adapted for other applications. For example, the needle assembly 16 may or may not include the needle hub 46 of the configuration illustrated. Additionally or alternatively, the vascular access systems of the present disclosure and invention may be adapted for use in injections rather than in cooperation with catheters.

FIG. 1 further illustrates that the extravascular system 10 may include an optional adapter housing 50. The adapter housing 50, when included, may be configured to cooperate with the tip shield 60, such as to accommodate the tip shield 60 during use of the extravascular system 10 and to activate the tip shield 60 when the needle 40 is being withdrawn from the catheter assembly 14. The adapter housing 50 is illustrated schematically in FIG. 1 representative of the variety of configurations the adapter housing may take in cooperating with aspects of the needle assembly 16 and the catheter housing 14. For example, the distal end 52 of the adapter housing 50 may be configured with Luer lock features (not shown) to cooperate with mating Luer lock features on the catheter hub 26. Similarly, the proximal end 54 of the adapter housing 50 may be adapted to coordinate with the needle hub 46 or other aspect of the needle assembly 16. The adapter housing 50 is yet another example of a suitable housing 36 within the scope of the present disclosure.

With continuing reference to FIG. 1, the needle tip 44 is illustrated as being housed within the tip shield 60. The tip shield 60 shown in FIG. 1 is representative of needle shield 60 within the scope of the present disclosure. As used herein, the term tip shield 60 shield refers to a structure that is adapted to be positioned adjacent to the needle tip 44 when the needle tip has been withdrawn, such as withdrawn from the catheter assembly 14 or a patient's vascular system, to encapsulate the needle tip 42.

Figure 2:
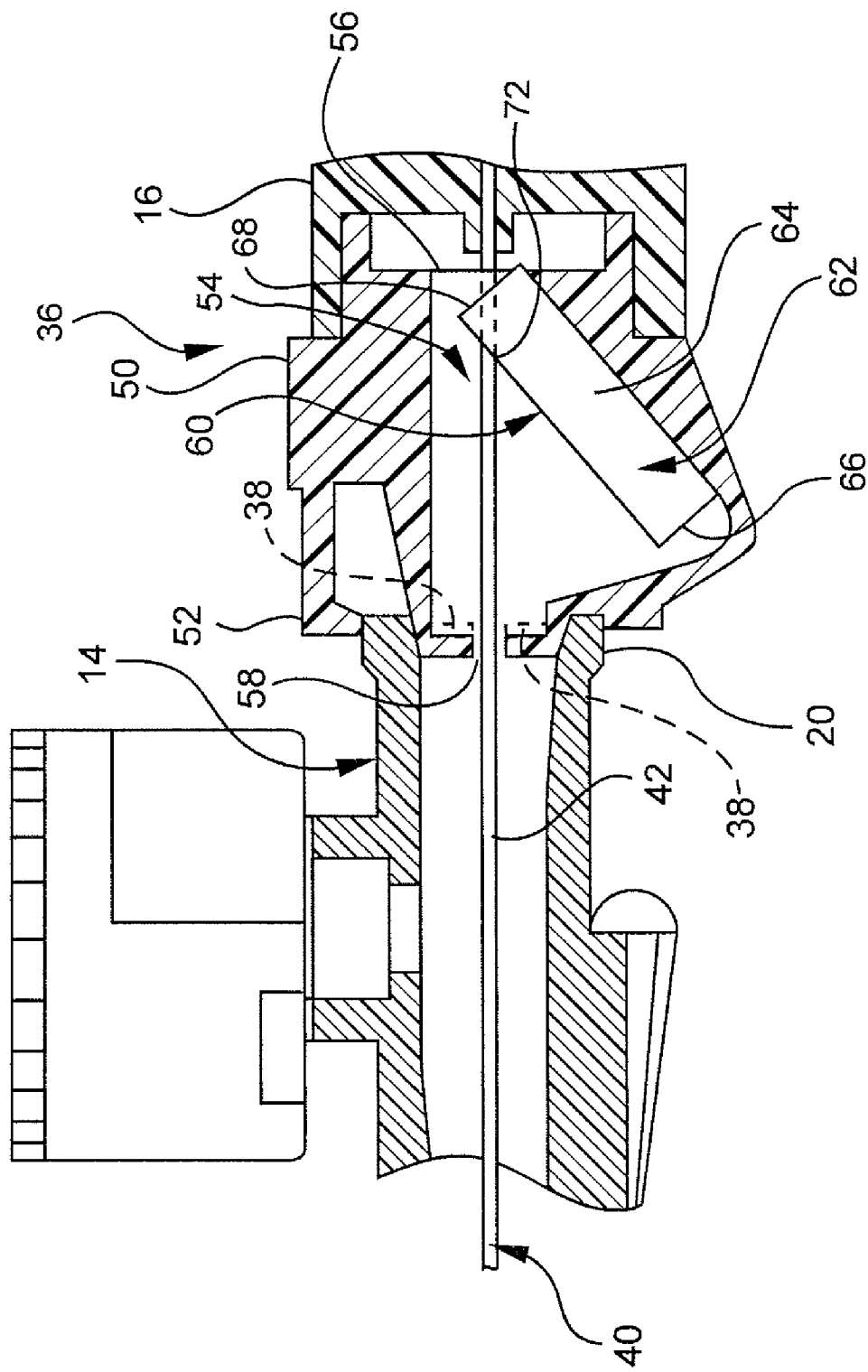
FIG. 2 is a cross-sectional view of a portion of an exemplary extravascular system.
Figure 3:
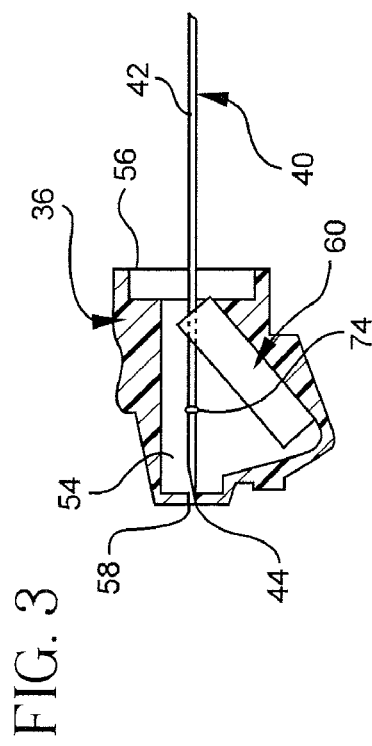
FIG. 3 is a cross-sectional view of a portion of a vascular access system showing an exemplary relationship between a housing, a tip shield, and a needle.

FIG. 2 provides an illustrative cross-sectional view of a portion of the extravascular system 10, including the catheter assembly 14, the adapter housing 50, and the needle assembly 16. As seen in FIG. 2, the catheter assembly 14 and the adapter housing 50 are adapted to associate proximal end 20 to distal end 52. Additionally, the proximal end of the adapter housing 50 associates with the distal end of the needle hub 46. The adapter housing 50 defines a passageway 54 having a proximal opening 56 and a distal opening 58. As shown in FIG. 3, the adapter housing 50 accommodates the tip shield 60 within the passageway 54.

Moreover, the proximal opening 56 of the housing 50 is configured to releasably retain the tip shield 60 within the housing. The retention of the tip shield 60 may be accomplished by disposing the side walls of the proximal opening 56 close enough together to create a frictional fit between the tip shield 60 and the proximal opening of the housing, as illustrated. Other suitable configurations may be utilized to releasably retain the tip shield 60 in the housing 50, such as disposing a yielding finger or other extension member into the path of the proximal opening 56 that allows the tip shield 60 to pass only under a certain minimum force. The releasable retention of the tip shield 60 may be implemented to limit or prevent the inadvertent separation of the needle assembly from the catheter assembly 14. Additionally or alternatively, the releasable retention of the tip shield 60 may be configured to assist in the activation or transition of the tip shield from a use position (as seen in FIG. 2) to a protection position (as seen in FIG. 1).

FIG. 2 further illustrates that extravascular system 10 may include one or more blood stabilizing materials 38 to further limit the risk of blood exposure. As seen in FIG. 2, the blood stabilizing material 38 is disposed inside the passageway 54 of the housing 50. Additionally or alternatively, blood stabilizing materials may be disposed inside or outside the adapter housing 50, inside and/or outside the tip shield 60, or in any other suitable location to control the spillage or flow of blood. The blood stabilizing material 38 is shown schematically to represent the variety of manners in which such material may be incorporated into the present vascular access systems and devices. The blood stabilizing material 38 may be a coagulant, an absorbent, or another material for stabilizing the blood to reduce the exposure risk. Similarly, the blood stabilizing material 38 may be a liquid, a solid, a gel, a powder, granular, or any other consistency appropriate for its use. The blood stabilizing material 38 may be disposed in a porous membrane or container (not shown) that allows the blood to enter while preventing the exit of the blood stabilizing material 38.

Once the blood has been stabilized by absorption and/or coagulation by contact with the blood stabilizing material 38, the risk of blood being splattered is significantly reduced and the exposure risk is still further minimized due to the stability of the blood (i.e., being coagulated or absorbed, the blood does not contaminate other objects or persons). The clinician is then left with a single, defined source of blood exposure risk at a distal exterior surface of the needle tip shield 60. The implementation of blood stabilizing material 38 together with the housing 36 configured to allow the tip shield to close before the needle 40 is completely withdrawn may further reduce the risk of blood exposure.

As suggested, the housing 36, whether implemented as part of a catheter assembly, as a separate adapter, or as part of a needle assembly, may be adapted to allow the tip shield 60 to close or otherwise entrap the needle tip 44 before the needle is fully withdrawn. FIG. 2 provides an exemplary illustration of a tip shield 60 including needle trap means configured to allow the needle shaft 42 to slide within the trap means while securing the needle tip 44 once it is withdrawn into the tip shield. For example, and as illustrated in FIG. 2, the tip shield 60 may include an enclosure 62 including at least one side wall 64, a closed distal end 66, and a proximal end 68. The proximal end may be adapted to slidingly engage the needle shaft 42, such as through an opening (not shown in FIG. 2). Similarly, at least a portion 64 of the side wall of the enclosure 62 may be adapted to slidingly engage the needle shaft 42. For example, a side wall may be provided with a needle shaft port 72 adapted to slidingly engage the needle shaft 42.

To prevent the needle 40 from being withdrawn proximally from the tip shield 60, thereby exposing the needle tip 44, at least one of the needle 40 and the tip shield 60 may be configured to retain the needle. For example, the needle shaft 42 may be provided with an enlarged shaft region 74 (seen in FIG. 3) proximate the needle tip 44 or the needle tip itself and the opening in the proximal end 68 of the enclosure 62 may be configured to prevent the complete withdrawal of the needle tip 44 from the tip shield 60 in the proximal direction. Additionally, the closed distal end 66 of the tip shield 60 prevents distal exit of the needle tip 44 from the tip shield 60 once the needle tip is disposed within the chamber 76 defined by the enclosure 62.

As will be described in further detail in connection with FIGS. 7-12, the tip shield 60 is configured to allow the needle shaft to extend through a sidewall 64 of the enclosure 62. Accordingly, with the needle shaft extending through the proximal end of the enclosure and the sidewall of the enclosure, the needle shaft is disposed at an angle with respect to the needle shaft. Depending on the configuration of the needle shaft port 72, the angle between the needle shaft and the tip shield may vary. One exemplary relationship is shown in FIG. 2.

Figure 4:
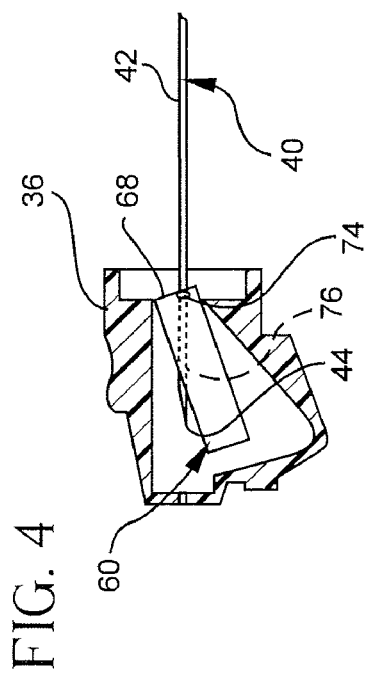
FIG. 4 is a cross-sectional view of the system of FIG. 3 shown with the needle further withdrawn from the housing.
Figure 5:
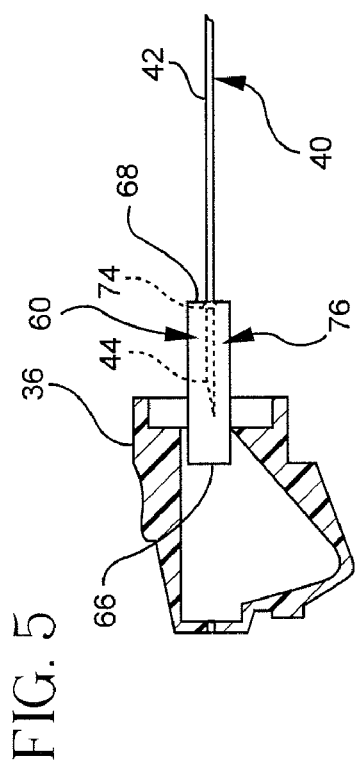
FIG. 5 is a cross-sectional view of the system of FIG. 3 shown with the needle completely withdrawn from the housing and the tip shield enclosing the needle tip.

Referring now to FIGS. 3-5 and 13 collectively, a cross-sectional view of a needle assembly 16 and a housing 36 are illustrated having the needle tip 44 and the tip shield 60 in various states of relationship with the housing 36. As illustrated, the housing 36 is representative of both an activating housing 34 as may be part of a catheter assembly 14 and an adapter housing 50, as well as other housing configurations that may be implemented. One exemplary manner through which the present tip shields 60 and vascular access systems 10 reduce and/or prevent needle sticks is illustrated in FIGS. 3-5. Other suitable methods and configurations may similarly be used implementing the principles of the present disclosure. As just one example, the tip shield 60 may be retained on the needle shaft 42 through use of a tether (not shown) coupled to the tip shield and the needle hub 46 where the tether is dimensioned to be shorter than the needle shaft.

FIG. 3 illustrates an exemplary relationship between the housing 36, the tip shield 60, and the needle 40 when the needle is being withdrawn but before the enlarged shaft region 74 has entered the tip shield. As discussed above, the needle tip 44 is being withdrawn proximally and is positioned adjacent the distal opening 58 of the housing 36. The needle shaft 42 extends through the proximal opening 56 of the housing 36, the proximal end 68 of the tip shield 60, and the sidewall 64 of the tip shield.

Referring now to FIG. 4, the needle 40 is shown being further withdrawn in the proximal direction. The enlarged shaft region 74, here illustrated as a ferrule, near the needle tip 42 has passed through the sidewall 64 of the tip shield and is shown engaged with the proximal end 68 of the tip shield. It is noted that the enlarged shaft region 74 may be provided by a ferrule or by other means. As the enlarged shaft region 74 engages the proximal end of the tip shield, the needle shaft is no longer able to slide through the tip shield and the tip shield position changes from the disposition shown in FIG. 3. As the needle is continually moved proximally relative to the housing, the needle shaft 42 and the tip shield 60 will try to move together. However, the proximal opening 56 of the housing 36 does not allow such movement without first moving the tip shield 60 relative to the needle shaft 42. As illustrated, the tip shield 60 rotates becoming more coaxial with the needle shaft. As the needle 40 and the tip shield 60 are drawn through the proximal opening 56 of the housing 36, the needle tip 44 is pressed further into the chamber 76 of the tip shield 60. The length of the tip shield 60 and the distance from the enlarged shaft region 74 to the needle tip 44 may be coordinated to allow the needle tip to be seated in or received by the tip shield. Any suitable length may be used while shorter lengths may be preferred for the convenience of the users and the costs of materials.

It should be noted by comparing the illustrations in FIGS. 3 and 4 that the needle shaft port 72 and the opening in the proximal end 68 may be configured to allow some movement of the needle shaft to accommodate the rotation of the tip shield relative to the needle shaft. For example, the opening in the proximal end of the tip shield may be configured as a slot having sufficiently narrow width to retain the needle tip in the chamber 76 and a length sufficient to accommodate the rotation of the tip shield. Similarly, the needle shaft port 72 or other opening in the sidewall 64 of the tip shield may be sized to allow such movement.

As the needle 40 and the tip shield 60 are further drawn through the proximal opening 56 of housing 36, the tip shield 60 continues to move relative to the needle shaft to a final position in which the needle tip 44 is pressed completely through the needle shaft port 72 into the chamber 76 of the tip shield to encapsulate the needle tip 44, which is best seen in FIG. 5. As illustrated in FIG. 5, the tip shield 60 is longer than the length of the needle 42 from the needle tip 44 to the enlarged shaft region 74. Thus, the needle tip 44 is fully encased within the tip shield 60.

The enlarged shaft region 74 together with the proximal end of the tip shield prevent the needle tip 44 from exiting the tip shield proximally while the closed distal end 66 of the tip shield prevents the need tip from exiting distally. As will be seen in the discussion of FIGS. 7-12, the opening in the sidewall 64 is configured to prevent exit of the needle shaft 42 and/or needle tip 44 once the needle tip is drawn into the chamber 76.

The releasable retention of the tip shield 60 by the housing 36 may be configured to ensure that the needle tip 44 is completely received into the chamber 76 before the needle is separated from the housing. Such a configuration ensures that the needle tip 44 is not exposed and thereby prevents needle sticks. Additionally, enclosing the needle tip 44 in the tip shield 60 before the needle tip 44 exits the housing may reduce the risk of blood exposure as well.

Figure 13:
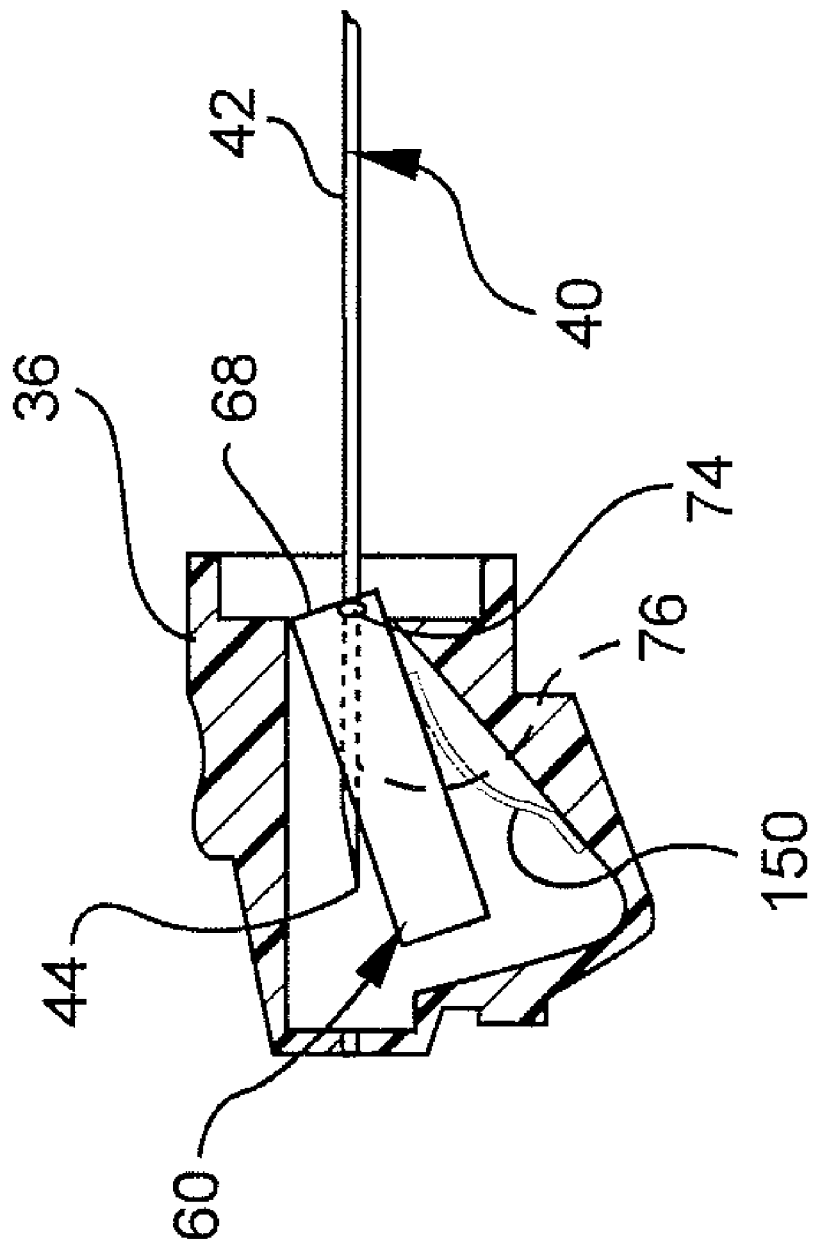
FIG. 13 is a cross-sectional view of another embodiment of the tip shield of the present invention.

FIG. 13 illustrates essentially the same device as illustrated in FIGS. 3-5, however, the device is provided with a leaf spring 150. Leaf spring 150 biases the tip shield 60 upwardly as the needle is withdrawn. The leaf spring 150 simply provides additional force in an upward direction to assure that the needle is ultimately encased within the tip shield 60.

Figure 6:
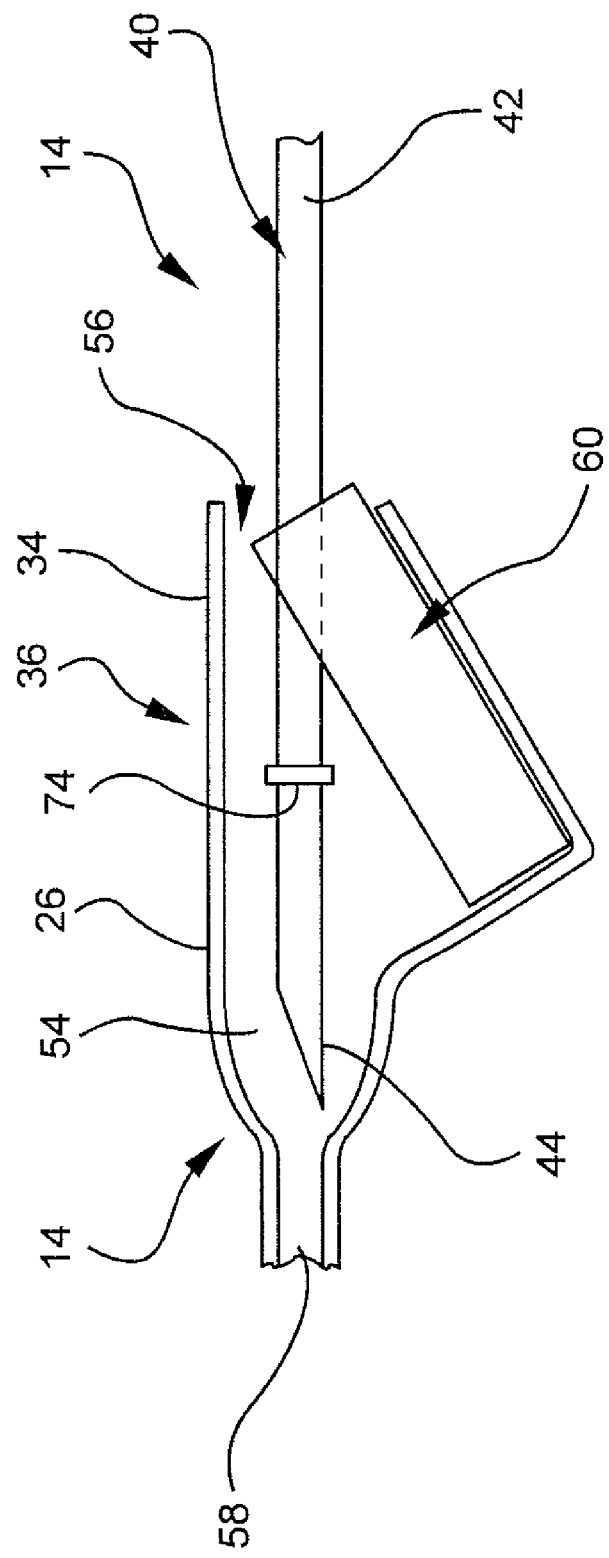
FIG. 6 is a schematic cross-sectional of a portion of an exemplary extravascular system.

FIG. 6 presents a cross-sectional view similar to the view of FIG. 3. FIG. 6 schematically illustrates a housing 36 configured as an activating housing 34 that is formed as part of the catheter assembly 14, or more particularly as part of the catheter hub 26. The elements and the relative positions of the elements are the same in FIG. 6 as they are in FIG. 3 and little more description is necessary. It should be noted that the proximal opening 56 of the activating housing 34 may be configured to releasably retain the tip shield 34 and to cause the tip shield to move into a protecting position that is at least substantially coaxial with the needle shaft. FIG. 6 is merely a schematic representation of a catheter hub 26 adapted to cooperate with tip shields of the present disclosure. Other suitable and more developed configurations may be used as well.

Figure 7:
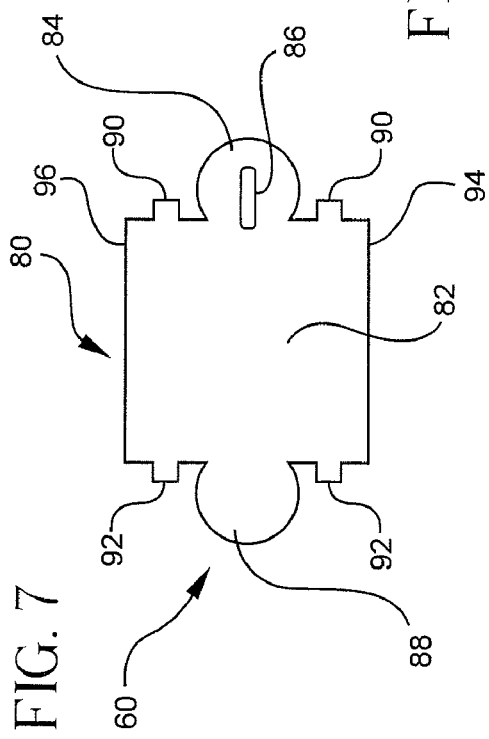
FIG. 7 is a top plan view of a tip shield shown in an unformed stage.
Figure 8:
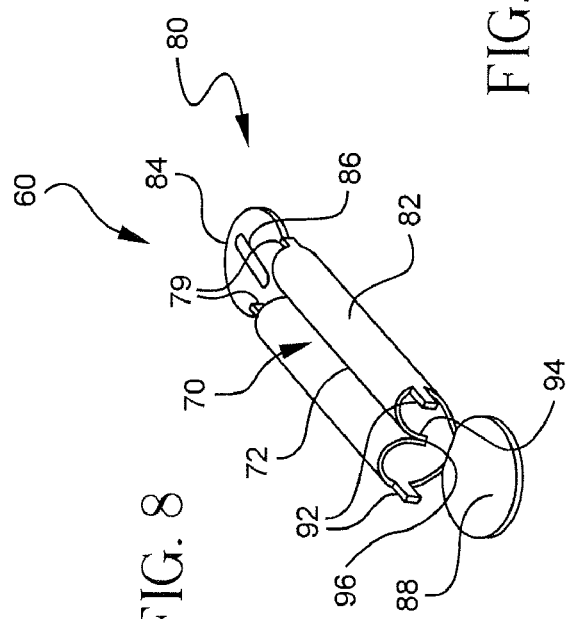
FIG. 8 is a perspective view of the tip shield of FIG. 7 shown in a partially-formed stage.
Figure 9:
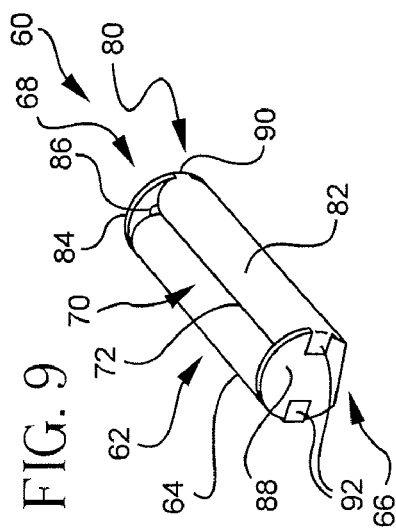
FIG. 9 a perspective view of the tip shield of FIG. 7 shown in a formed stage.

Turning now to FIGS. 7-12, additional details of the tip shield are provided along with various examples of methods of constructing the tip shield. For example, FIGS. 7-9 provide top plan and perspective views of the tip shield 60 at various stages of the manufacturing process. The tip shield may be made of any suitable material that is resistant to penetration by a needle tip. In the illustrated configuration of FIGS. 7-9, the tip shield 60 is made from a stamped sheet 80 (FIG. 7) of stainless steel or other suitable, non-corroding metal or plated metal. The sheet 80 includes a rectangular body 82, a dependent proximal disk 84 with a slot 86 or other opening of a length sufficient to allow the tip shield 60 to pivot relative to the needle shaft 42, as discussed above, and a width to closely slidably receive the shaft 42 of needle 40 but to not pass the enlarged shaft region 74. The sheet 80 further includes a dependent distal disk 88, a pair of proximal tabs 90, and a pair of distal tabs 92. The tabs 90, 92 are optional, but may be used to facilitate the formation of the tip shield 60, as seen in FIG. 9. Alternatively, the proximal and distal disks may be coupled and joined to the body through other means.

The body 82 of sheet 80 is rolled to form a substantially cylindrical shape, as seen in FIG. 8. The opposing longitudinal edges 94 and 96 (shown in FIG. 7) are brought together and rolled inward into the cylinder forming what may be referred to as having a rounded heart-shaped cross-section. The inwardly rolled opposing longitudinal edges are one manner of forming an opening in the sidewall 64 through which the needle shaft 42 may extend. The opposing longitudinal edges may form one example of a needle shaft port 72. The longitudinal edges 94, 96 may be disposed to be touching or at a spacing that is smaller than the diameter of the needle shaft 42. Accordingly, the needle 40 cannot pass through the needle shaft port 72 without deforming the body 82 of the tip shield 60. The material and thickness thereof from which the sheet 80 is made, material properties, bending/forming geometry, the spacing of the edges 94, 96, heat treatment or temper of the material, and contour (sharp, tapered, or rounded) of the edges 94, 96 can be varied as desired to control resistance due to drag as the needle 40 is drawn through the needle shaft port 72.

While opposing longitudinal edges 94, 96 may be used to form the needle shaft port 72, other suitable configurations may be used. For example, the needle shaft port 72 may include deforming or biased materials, such as plastics, that allow the needle shaft to move in one direction (e.g. to allow the needle tip to be drawn in to the chamber) but not in the other direction (e.g. to allow the needle tip to be moved out of the chamber).

The proximal end 68 and distal end 66 of the tip shield are closed by the respective proximal and distal disks 84 and 88, which may be as seen in FIG. 9. This may be accomplished by bending the proximal and distal disks 84, 88 ninety degrees and securing using the proximal and distal tabs 90, 92. Additionally or alternatively, the disks 84, 88 may be secured to the body 82 through other means. As illustrated in FIG. 9, the tip shield 60 defines a tip-receiving chamber 76 of a length slightly larger than the distance from the enlarged shaft region 74 to the needle tip 44 to receive the needle tip 44 and enlarged shaft region 74 therein.

While the opening in the proximal end 68 of the tip shield 60 is illustrated as a relatively narrow slot 86, the opening may be configured in any suitable manner. For example, to facilitate assembly of the needle assembly, the opening in the proximal end 68 and/or the enlarged shaft region 74 may be configured to facilitate the passage of the enlarged shaft region distally and to retain or prevent the enlarged shaft region during proximal movement. Additionally or alternatively, the construction or assembly of the needle assembly 16 may be facilitated through strategic order of operations, such as inserting the needle in the reverse direction so that the enlarged shaft region does not have to pass through the tip shield in a distal direction. Other suitable methods for assembling the components of the present disclosure are available.

Figure 10:
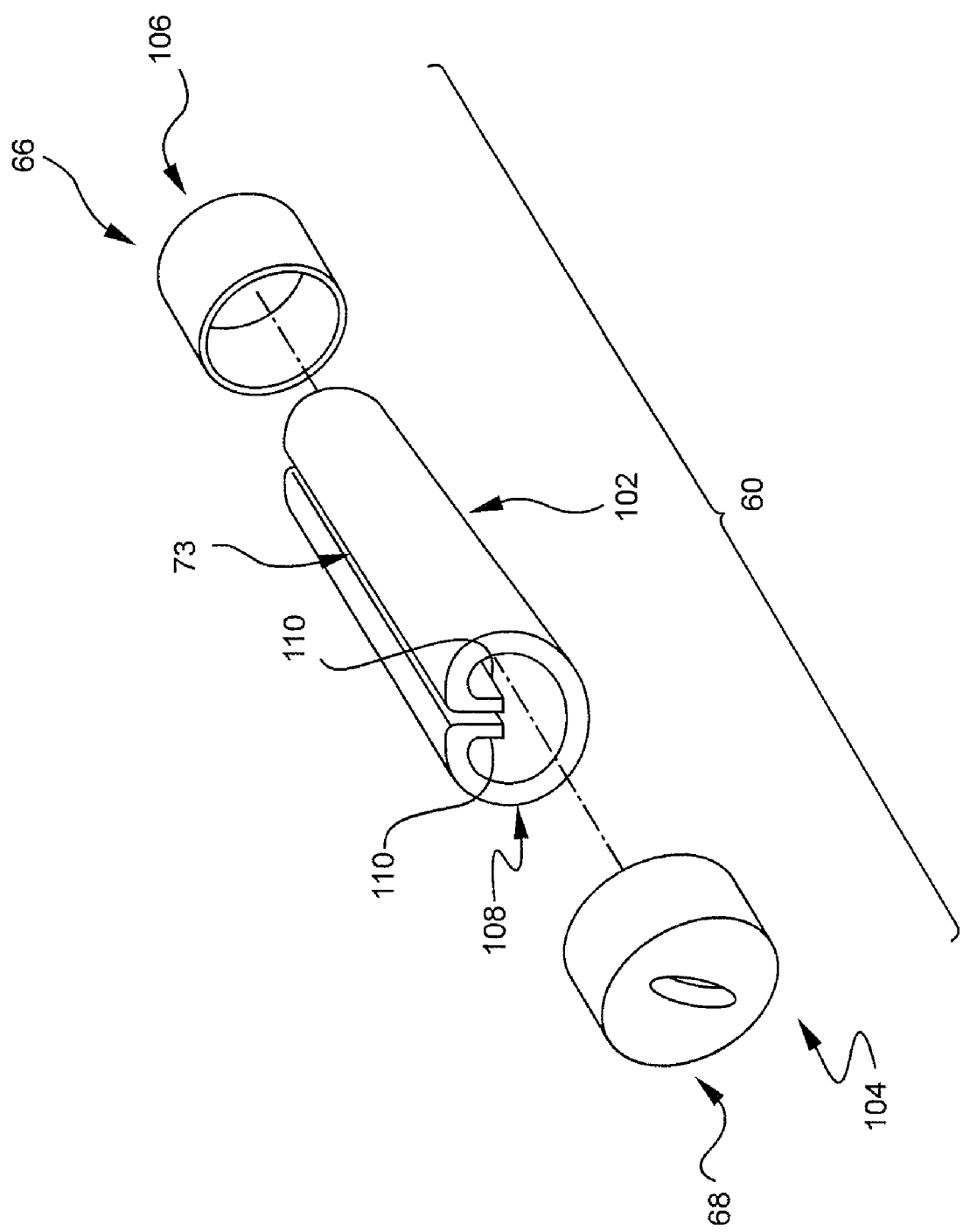
FIG. 10 is an exploded perspective view of an alternative tip shield molded from a plastic material.

Referring to FIG. 10, an exploded perspective view of an alternative tip shield 60 that includes a body 102, a proximal end cap 104, and a distal end cap 106 each molded from a suitable medical grade plastic material. The body 102 is extruded or otherwise formed to provide a hollow cylinder 108 of the substantially cylindrical construction illustrated. The substantially cylindrical cross-section includes an opening in the sidewall thereof, which may be provided by a pair of opposing longitudinal edges 110. Additionally or alternatively, the plastic tip shield may be molded to provide a more customized needle shaft port 73. Due to the flexibility and customizability of plastics, a variety of options may be available for use of plastic as tip shields. For example, the plastic materials may be adapted to provide a better seal against re-emergence of the needle tip and/or to facilitate the operation of the present extravascular systems 10.

The proximal end 68 and the distal end 66 of the tip shield may be capped by adhesively or ultrasonically affixing the proximal and distal end caps 104 and 106 thereto. In addition, the body 102 may be constructed of two halves which are joined together by sonic welding, adhesives, snap fitting, or any other attachment mechanism. The plastic material and thickness(es) of the material from which the body 102 is made, material properties, bending/forming geometry, the spacing between edges, any filler materials added to the plastic material, and the contour (sharp, tapered, or rounded) of the edges can be varied as desired to control resistance due to drag as the needle 40 is drawn through the valve needle shaft port 73.

Figure 12:
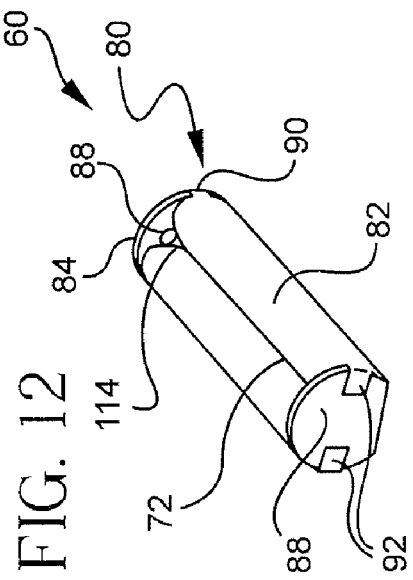
FIG. 12 is a perspective view of the tip shield of FIG. 11 shown in a formed stage.
Figure 11:
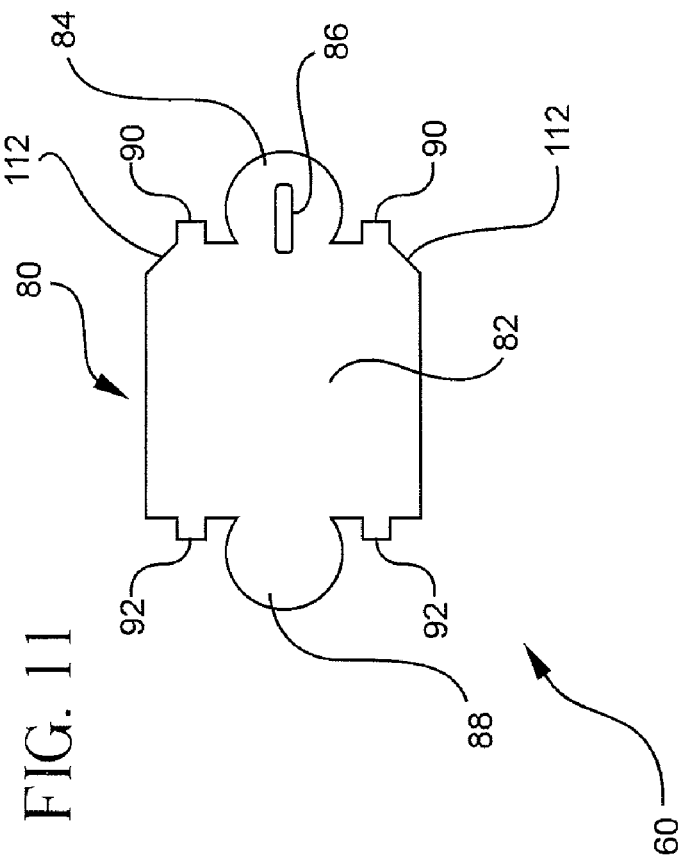
FIG. 11 is a top plan view of a tip shield shown in an unformed stage.

FIGS. 11 and 12 provide a schematic illustration of yet another variation on the inventive concepts described herein. FIG. 11 is comparable to FIG. 7 illustrating that the tip shield 60 may be formed from a sheet 80 of metal or other suitable material. However, it should be noted that the body 82 of the tip shield 60 shown in FIG. 11 includes shaped regions 112 adjacent the proximal end cap 104. Referring to FIG. 12, which illustrates the tip shield 60 formed from the sheet 80 of FIG. 11, it can be seen that the shaped regions 112 cooperate to form an enlarged opening 114 in the needle shaft port 72. The enlarged opening 114 may be sized to reduce the frictional resistance against movement of the needle shaft in the needle shaft port 72. Accordingly, the shaped regions 112 may be configured in any suitable manner to create an enlarged opening 114 suitable for the needle assembly being used (e.g., the enlarged opening 114 may be larger for larger diameter needle shafts).

Various modifications to the needle tip shields of the present invention are possible while staying within the same inventive concept. For example, the tip shields can be used to protect the tip of any type of sharp, including a cannula in an IV catheter, the tip of a stylet in a long anesthesia needle, a hypodermic needle, surgical blade and other such medical devices. Additionally, the cross-section of the tip shield can be of other shapes such as square, rectangular, triangular, oval, polygonal, and the like.

Still additionally or alternatively, the needle shaft port in the tip shield body can be formed by slitting a pliable tube. In some configurations, the needle shaft port may be held open by a tab or a post-like feature, such as adjacent to the proximal end of the tip shield. The tab or post-like feature may be used in connection with any of the tip shields described above and may be associated with the housing 36 or other component of the vascular access system. The use of a tab feature to hold the needle shaft port open may reduce the frictional drag on the needle shaft as it is being withdrawn and may enable the tip shield to more completely seal once the tip is received in the chamber and the tab feature is disengaged from the tip shield allowing the needle shaft port to close.

Additionally or alternatively, the enlarged shaft region of the needle may be non-symmetrical and/or may be formed other than by crimping the shaft or affixing a ferrule. Moreover, the enlarged shaft region can be retained to prevent proximal movement beyond the tip shield proximal end by means other than the restricted width of the slot.

As still further variations on the inventive principles of the present application, the means for activating the tip shield may be varied in any suitable manner. For example, in addition to or as an alternative to the restricted opening of the housing and cooperating inclined slope (see FIGS. 2-6), the needle tip can be pressed or introduced into the chamber of the tip shield by pressure from a biasing member encouraging the tip shield towards the needle shaft.

It is believed that the disclosure set forth above encompasses multiple distinct methods and/or apparatus with independent utility. While each of these methods and apparatus has been disclosed in its preferred form, the specific embodiments thereof as disclosed and illustrated herein are not to be considered in a limiting sense as numerous variations are possible. The subject matter of the disclosures includes all novel and non-obvious combinations and sub-combinations of the various elements, features, functions and/or properties disclosed herein. The principles of the present disclosure may be embodied in other specific forms without departing from its structures, methods, or other essential characteristics as broadly described herein, The described embodiments are to be considered in all respects only as illustrative, and not restrictive. The scope of the disclosure is, therefore, not limited by the foregoing description or the following claims, and all changes that come within the meaning and range of equivalency of the foregoing description and/or the following claims are to be embraced within its scope. Similarly, where the description and/or the claims recite "a" or "a first" element or the equivalent thereof, such description should be understood to include incorporation of one or more such elements, neither requiring nor excluding two or more such elements.

It is believed that the following claims are directed to certain combinations and sub-combinations that correspond to disclosed examples and that are believed to be novel and non-obvious. Other combinations and sub-combinations of features, functions, elements and/or properties may be claimed through amendment of the present claims or presentation of new claims in this or a related application. Such amended or new claims, whether they are directed to a different combination or directed to the same combination, whether different, broader, narrower or equal in scope to the original claims, are also regarded as included within the subject matter of the present disclosure.

The invention claimed is:

1. A vascular access system for preventing injury, comprising:
   a sharp having a shaft that terminates at a tip;
   a tip shield having an enclosure defining a chamber, wherein the enclosure includes at least one side wall configured to slidably engage the shaft, a closed distal end, and a proximal end slidably engaging the shaft;

a housing defining a passageway with respective proximal and distal openings through which said sharp slidably extends, wherein the proximal opening of the housing releasably retains the tip shield in the passageway; and wherein the sharp includes a region proximate to the tip, wherein the tip shield proximal end includes an opening adapted to slidably engage the shaft without allowing the region to pass proximally through the opening, and wherein the tip shield secures the tip in the chamber upon withdrawal of the tip into the chamber.

2. A vascular access system as defined in claim 1, wherein the proximal opening of the housing frictionally retains the tip shield to allow insertion of the tip shield into the passageway of the housing upon application of a nominal force and to prevent inadvertent withdrawal of the tip shield from the passageway.

3. A vascular access system as defined in claim 1, wherein at least one of the housing and the tip shield includes blood stabilizing materials.

4. A vascular access system as defined in claim 1, wherein the shaft region includes an enlarged region proximate to the tip.

5. A vascular access system as defined in claim 1, wherein the tip shield comprises an elongate hollow body defining the chamber and a shaft port, a proximal end wall at the proximal end of the tip shield with a pivot hole that slidably and pivotally engages the shaft, and a distal end wall at the distal end of the tip shield; and wherein the shaft extends through the pivot hole and the shaft port when the sharp is disposed in the housing disposing the tip shield at an angle with the shaft.

6. A vascular access system as defined in claim 5, wherein the pivot hole of the proximal end wall engages the enlarged shaft region during proximal movement of the sharp relative to the housing and further proximally movement of the sharp relative to the housing causes the tip shield to pivot at the pivot hole drawing the tip into the needle shaft port and into the chamber.

7. A vascular access system as defined in claim 5, wherein the housing includes a finger extending into the passageway and engaging the shaft port to open the port facilitating sliding movement of the shaft within the port as the sharp is withdrawn from the housing.

8. A vascular access system as defined in claim 5, wherein the housing includes a biased member configured to bias the tip shield toward the shaft as the needle is moved proximally relative to the house to draw the tip into the shaft port and into the chamber.

9. A vascular access system as defined in claim 1, wherein the tip shield enclosure includes a body having opposing longitudinal edges and defining a substantially cylindrical cross-section, wherein the body is configured to engage the shaft and includes a shaft port comprising the opposing edges of the body disposed in a spaced apart relationship to allow the shaft to enter the chamber and to prevent emergence of the tip from the chamber.

10. A vascular access system as defined in claim 9, wherein the tip shield is formed from a stamped sheet of metal that includes a body of generally rectangular shape and respective dependent proximal and distal disks adapted to form proximal and distal end walls, the body being rolled to form the substantially cylindrical cross-section and shaft port, and the disks being bent ninety degrees to abut the substantially cylindrical body.

11. A vascular access system as defined in claim 9, wherein the body is extruded from plastic material and includes opposing longitudinal edges, wherein the proximal and distal ends of the tip shield are covered by respective end caps of plastic material.

12. A vascular access system as defined in claim 11, wherein the proximal and distal end caps are affixed to the body using a process chosen from the group consisting of adhesive and ultrasonic welding.

13. An extravascular system for accessing the vasculature of a patient, comprising:

a catheter assembly that defines a lumen extending from an opening at a distal end thereof to a catheter hub at a proximal end thereof;

a needle assembly that includes a needle hub disposed at a proximal end of a needle having a shaft disposed within said lumen defined by said catheter assembly, a needle tip extending from the opening of the catheter assembly, and an enlarged shaft region proximate to the needle tip;

a tip shield having an enclosure defining a chamber, wherein the enclosure includes a needle shaft port configured to slidably engage the needle shaft, a closed distal end, and a proximal end having an opening slidably engaging the needle shaft while preventing the enlarged shaft region from passing proximately through the opening;

a housing defining a passageway with respective proximal and distal openings through which said needle slidably extends, wherein the proximal opening of the housing releasably and frictionally retains the tip shield in the passageway to allow insertion of the tip shield into the passageway of the housing upon application of a nominal force and to prevent inadvertent withdrawal of the tip shield from the housing; and wherein the needle shaft extends through the opening of the tip shield and the needle shaft port disposing the tip shield at an angle with the needle shaft, wherein the opening in the proximal end of the tip shield engages the enlarged shaft region during proximal movement of the needle relative to the housing, and wherein further proximal movement of the needle relative to the housing causes the tip shield to pivot drawing the needle tip into the needle shaft port and into the chamber, disposing the tip shield coaxially with the needle shaft.

14. A needle assembly for preventing needle sticks, comprising:

a hypodermic needle having a needle shaft that terminates at a needle tip;

a tip shield having an enclosure defining a chamber, wherein the enclosure includes a body, a proximal end, a closed distal end, and a needle trap means that slidably engages the needle shaft, wherein the needle trap means secures the needle tip in the chamber upon withdrawal of the needle tip into the chamber;

housing means for releasably retaining the needle and the tip shield; and wherein withdrawal of the needle from the housing means causes said needle tip to be engaged by the needle trap means and secured within the chamber wherein the needle includes a retention means for preventing the needle from passing proximally past the proximal end of the tip shield, and wherein the needle trap means includes a needle shaft port defined by the body the enclosure and a pivot hole at the proximal end of the tip shield, wherein the needle shaft extends through the pivot hole and the needle shaft port disposing the tip shield at an angle with the needle shaft, wherein the pivot hole engages the retention means during proximal movement of the needle relative to the housing means, and wherein further proximal movement of the needle relative to the housing means causes the tip shield to pivot drawing the needle tip into the needle shaft port and into the chamber, disposing the tip shield coaxially with the needle shaft.

15. A needle assembly as defined in claim 14, wherein the housing means comprises a passageway with respective proximal and distal openings through which the needle slidably extends, wherein the proximal opening of the housing means frictionally retains the tip shield to allow insertion of the tip shield into the passageway of the housing upon application of a nominal force and to prevent inadvertent withdrawal of the tip shield from the passageway.

16. A method for preventing needle sticks upon withdrawal of a hypodermic needle, comprising the steps of:
   providing a needle assembly having a hypodermic needle, a tip shield, and a housing, wherein the needle includes a needle shaft that terminates at a needle tip and an enlarged needle shaft region proximate to the needle tip, wherein the tip shield includes an enclosure defining a chamber, wherein the enclosure includes a needle shaft port configured to slidably engage the needle shaft, a closed distal end, and a proximal end having an opening slidably engaging the needle shaft while preventing the enlarged shaft region from passing proximately through the opening; wherein the housing defining a passageway with respective proximal and distal openings through which said needle slidably extends, wherein the proximal opening of the housing releasably retains the tip shield in the passageway;
   passing the needle distally through the housing to engage the patient's vascular system;
   withdrawing the needle from the housing to cause the enlarged shaft region to engage the opening in the proximal end of the tip shield to move the needle tip through the needle shaft port and into the chamber; and
   further withdrawing the needle from the housing to cause the tip shield to pass through the proximal opening of the housing.

17. A method for preventing needle sticks as defined in claim 16, wherein the needle shaft port is disposed on a side wall of the enclosure disposing the tip shield at an angle with the needle shaft when the tip shield is disposed in the housing, and wherein further proximal movement of the needle relative to the housing following engagement of the enlarged shaft region with the proximal end opening causes the tip shield to pivot drawing the needle tip into the needle shaft port and into the chamber.

\* \* \* \* \*